United States Patent [19]

Hock

[11] Patent Number: 5,190,042
[45] Date of Patent: Mar. 2, 1993

[54] APPARATUS FOR DETERMINING INTRAOCULAR PRESSURE

[75] Inventor: Bertram Hock, Haibach, Fed. Rep. of Germany

[73] Assignee: Datron-Electronic GmbH, Muhltal-Traisa, Fed. Rep. of Germany

[21] Appl. No.: 583,730

[22] Filed: Sep. 14, 1990

[30] Foreign Application Priority Data

Sep. 22, 1989 [DE] Fed. Rep. of Germany ........ 3931630

[51] Int. Cl.$^5$ ................................................. A61B 3/16
[52] U.S. Cl. ..................................... 128/652; 128/645
[58] Field of Search ................. 128/645, 646, 647, 652

[56] References Cited

U.S. PATENT DOCUMENTS

| | | | |
|---|---|---|---|
| 3,446,061 | 5/1969 | Draeger et al. | 128/652 |
| 3,470,736 | 10/1969 | Bartfay | 128/652 |
| 4,192,317 | 3/1980 | Munnerlyn et al. | 128/646 |
| 4,213,464 | 7/1980 | Katz et al. | 128/652 |
| 4,344,037 | 8/1982 | Ragsdale | 328/114 |
| 4,523,597 | 6/1985 | Sawa et al. | 128/652 |
| 4,621,644 | 11/1986 | Eilers | 128/652 |
| 4,665,923 | 5/1987 | Kobayashi | 128/648 |

FOREIGN PATENT DOCUMENTS

| | | |
|---|---|---|
| 547087 | 3/1974 | Switzerland . |
| 748282 | 4/1956 | United Kingdom ............. 128/652 |
| WO88/03384 | 5/1988 | World Int. Prop. O. . |

*Primary Examiner*—Randy C. Shay
*Attorney, Agent, or Firm*—Darby & Darby

[57] ABSTRACT

To determine intraocular pressure with a tonometer in which a measurement prism presses against the human eye with a given force and a corresponding relationship is established between the force and the area aplanated thereby, it is proposed that a plurality of measured values of force and aplanated area, each being associated with the other, be determined per unit of time during the course of a continuous increase in pressure by means of the power-driven, spring-pretensioned motion of the measurement prism and processed in the form of a curve in such a manner that the intraocular pressure can be determined differentially from the plurality of measured values.

18 Claims, 10 Drawing Sheets

APPARATUS FOR DETERMINING INTRAOCULAR PRESSURE

BACKGROUND OF THE INVENTION

Generally speaking, the present invention relates to the field of fine measurement; when properly handled, it enables force to be measured independently of position, especially by means of a so-called tonometer, whereby the gravitational forces that are present during every measurement process having no bearing on the results or can, at least, be taken into consideration through appropriate measures in the hardware or software.

To measure the intraocular pressure of patients, it is customary practice, following a general underlying principle, to press a suitable plane member against the eyeball, which is assumed to be of spherical configuration, and to measure the pressure which must be exerted to produce a given diameter of the circular area aplanated thereby when this given diameter is attained.

In a known device, a lever which can be pivoted about a stationary fulcrum is employed in this connection; this lever performs an arc-based pivotal motion toward the eye beneath a forehead support (to achieve a fixed position) and can therefore be pressed against the eye with a measurable exertion of force. At the opposite end of the lever on the other side of the fulcrum, an electric motor engages via a comparatively soft spring, thus implementing the advancement toward the eye that is required for performance of the measurement.

In a known measurement apparatus of this type, suspension of the pendulum-like lever can be problematic, as it describes an arc as a result of its fulcrum mounting. Nor is the possibility able to be excluded that measurement errors could occur as a result of the lack of dynamic balancing. Moreover, miniaturization efforts are quickly exhausted with pendulum apparatuses of this type.

Moreover, a tonometer has already been proposed (in unprepublished German Patent Disclosure Document No. 3,818,434) in which a first measurement slide and a second counter-slide are disposed on both sides of bearing rollers, the slides performing a mechanically coupled opposite motion one relative to the other, whereby the effect of the measurement slide and the counter-slide pressing against the bearing rollers is produced by an alternating magnetic effect exerted one upon the other. The two slides can therefore perform a free, opposite displacement motion, without being hindered by the respectively acting weight. The measurement slide then mounts a sensor head in the form of a prism, whose reflection properties are altered through the aplanation of the eyeball when pressure is exerted, and are identified by a photosensitive element, and are exploited for producing a signal when a given aplanation diameter is attained.

To this extent, all previously known tonometer systems are based upon the principle of performing an individual measurement, whereby it is agreed that this individual measurement is performed when an aplanation diameter of exactly 3.06 mm has been attained; empirical studies have shown this value to be particularly suitable, especially since various influencing factors more or less mutually offset one another in a given range, for example adhesion force and diaphragm stiffness (paper by Goldmann and Schmitt in DE-Ophthamalogica, 134, 1957).

In addition, it must also be taken into consideration that the best possible decoupling of the parameters of tear fluid volume and aplanated area can be achieved in such measurements, whereby it has also already been proposed that a so-called zero aplanation be performed in order to determine a volume of tear fluid which is then included in the determination of the area by means of a compensation calculation. However this always involves the necessity of performing individual measurements (such as for zero aplanation and for the above-mentioned diameter of 3.06 mm), which can involve serious errors merely as a result of the effect of random errors, whereby incorrect behavior on the part of the examinee at the moment the measurement is performed can also seriously falsify the measurement results.

SUMMARY OF THE INVENTION

It is therefore the object of the present invention to suggest a possibility for determining intraocular pressure which is able to always supply surprisingly perfect and, especially, highly accurate measurement results, without posing any significant burden on the examinee and without the necessity of having to include the imponderabilities of various origin which occur in the case of individual measurements and which falsify the measurement results.

The present invention solves this object and offers the advantage that, through the implementation of an entirely different measurement method, it is successful in minimizing the influence of random errors in that a plurality of measurements are performed per unit of time, whereby one function value, namely the force acting upon the eyeball, is continuously altered and, through a suitable measurement, are simultaneously stored in tabular form together with the correspondingly altering aplanation diameter of the eye in this correlated form, so that it is possible to record a type of aplanation function.

In this connection, it is advantageous to utilize a comparatively broad spectrum of aplanation diameters in which the various influencing factors mutually offset one another virtually completely so that the intraocular pressure can be correctly determined within this spectrum through measurement if the measured force is placed into relationship with the measured area. For this purpose, the preferred range of aplanation diameters is slowly traversed during the multiple measurements according to the present invention, and all force values determined in a random manner per unit of time are stored in a table as a function of the areas which are also determined, whereupon it is then possible to analyze the measurement, in accordance with this actual curve, which represents a characteristic curve with a plurality of measured values, through the formation of a differential coefficient, i.e. to determine the intraocular pressure differentially from the measured values which have been recorded. In this connection, through the recorded table values which are stored in a memory of sufficient size of a microcomputer, for example, it is also possible to plot a compensating straight line, in whose slope the intraocular pressure to be determined is implicitly contained.

Through an approach of this nature, it is additionally possible to define a force offset, which manifests itself in the form of a possible positioning error, as well as the area offset, which is caused by tear fluid, and to eliminate them through appropriate calculations.

It is especially advantageous for the prism forming the measurement member to be suspended absolutely free of friction, with the force exerted on the eye by the prism being determined through the deflection of a spring which, in turn, is optically measured in a manner that produces absolutely no influencing factors.

Parallelogram guidance, ultimately of the measurement member (prism), which is simultaneously implemented by the bearing spring, ensures good linear guidance of the measurement member relative to the measurement travel and, through its own design, prevents, or optimizes, the influence of any minimal lateral motions when the measurement member is deflected.

The completely friction-free suspension of the measurement member can also result in minor oscillating motions during the measurement process, whereby, through the complete electronic analysis of the measurement curve (aplanation area or diameter a function of the force exerted), such statistical oscillations about the actual curve are readily taken into consideration and eliminated in the software by the multiple measurements which are implemented through the present invention; in addition thereto, however, it is also possible to minimize the oscillation of the sensor with the measurement spring through suitable mechanical attenuation, for example through air chambers or attenuation through eddy-current brakes.

The overall new underlying concept of a tonometer that is presented here additionally results in a plurality of further advantages, each of which will then be discussed in conjunction with the following description for reasons of clarity.

BRIEF DESCRIPTION OF THE DRAWING

The above discussed and other objects, features and advantages of the present invention will become more apparent from the following description thereof, when taken in connection with the preferred practical examples shown in the accompanying drawings, in which.

DESCRIPTION OF THE PREFERRED EMBODIMENTS

Figure 1:
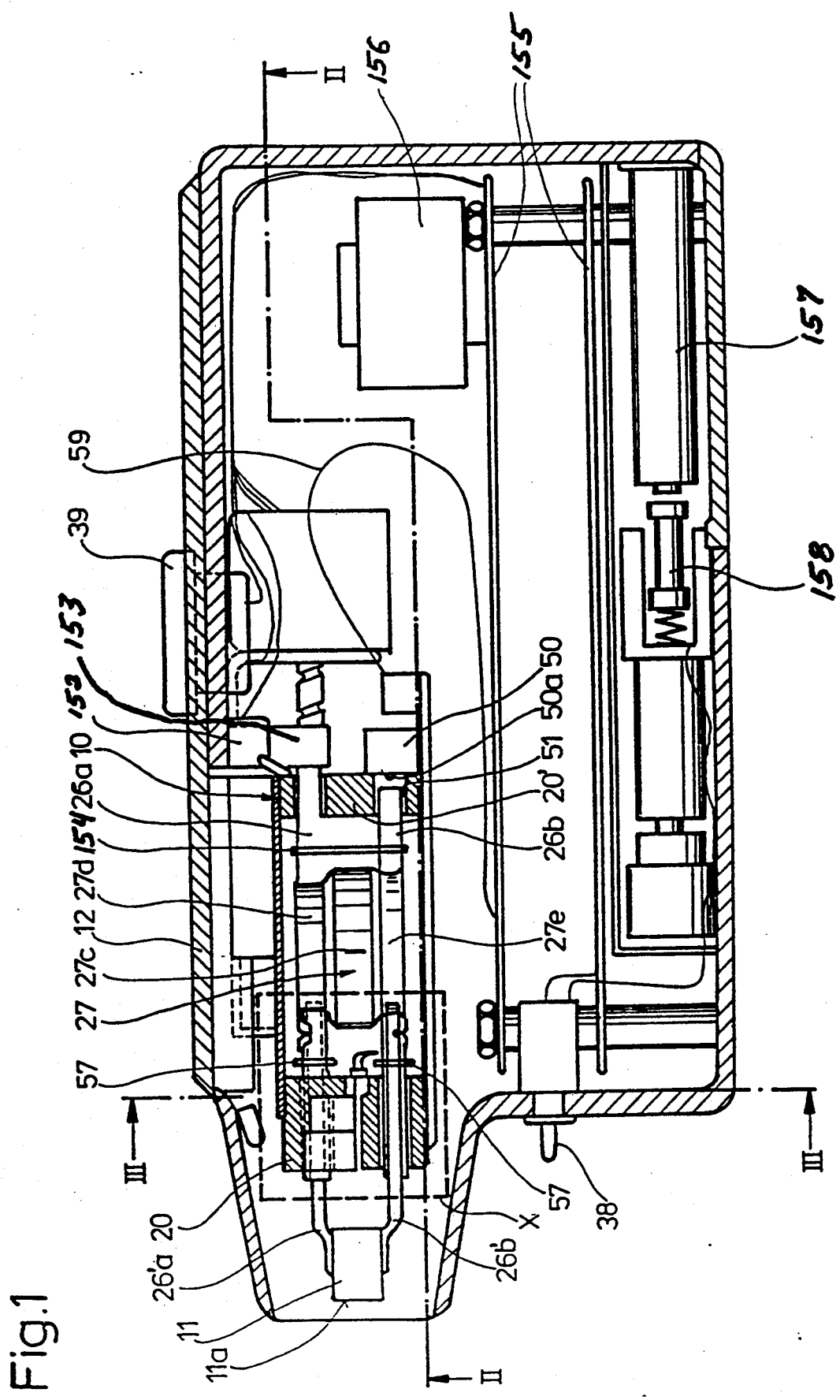
FIG. 1 shows the special measurement apparatus of an embodiment of the tonometer according to the present invention, contained in a housing, in a first longitudinal section taken along Line I—I in FIG. 3.

Referring now to the drawings, where like reference numerals designate like parts throughout the several views, the underlying concept of the present invention is based upon the realization that only by obtaining continuous measured values, corresponding to the portrayal of a plurality of correlated table values in curve form, is it possible at all to master the various parameters, which are sufficiently known to those with skill in the art and some of which result in considerable measurement errors, in such a manner as to avoid individual measurements, which are greatly influenced by random errors, and to always achieve a highly precise final result.

Consequently, the measurement apparatus according to the present invention provides the opportunity of being able to continuously increase the force acting upon the eyeball so that, in conjunction with ongoing measurement of the respective momentary aplanation value, an aplanation function can ultimately be obtained from which the intraocular pressure can then be determined differentially on the basis of the plurality of measured values recorded. This, alone, results in the significant advantage with respect to the impact of random errors which, as is known in and of itself, decline with the square root of the number of measurement points.

Figure 2:
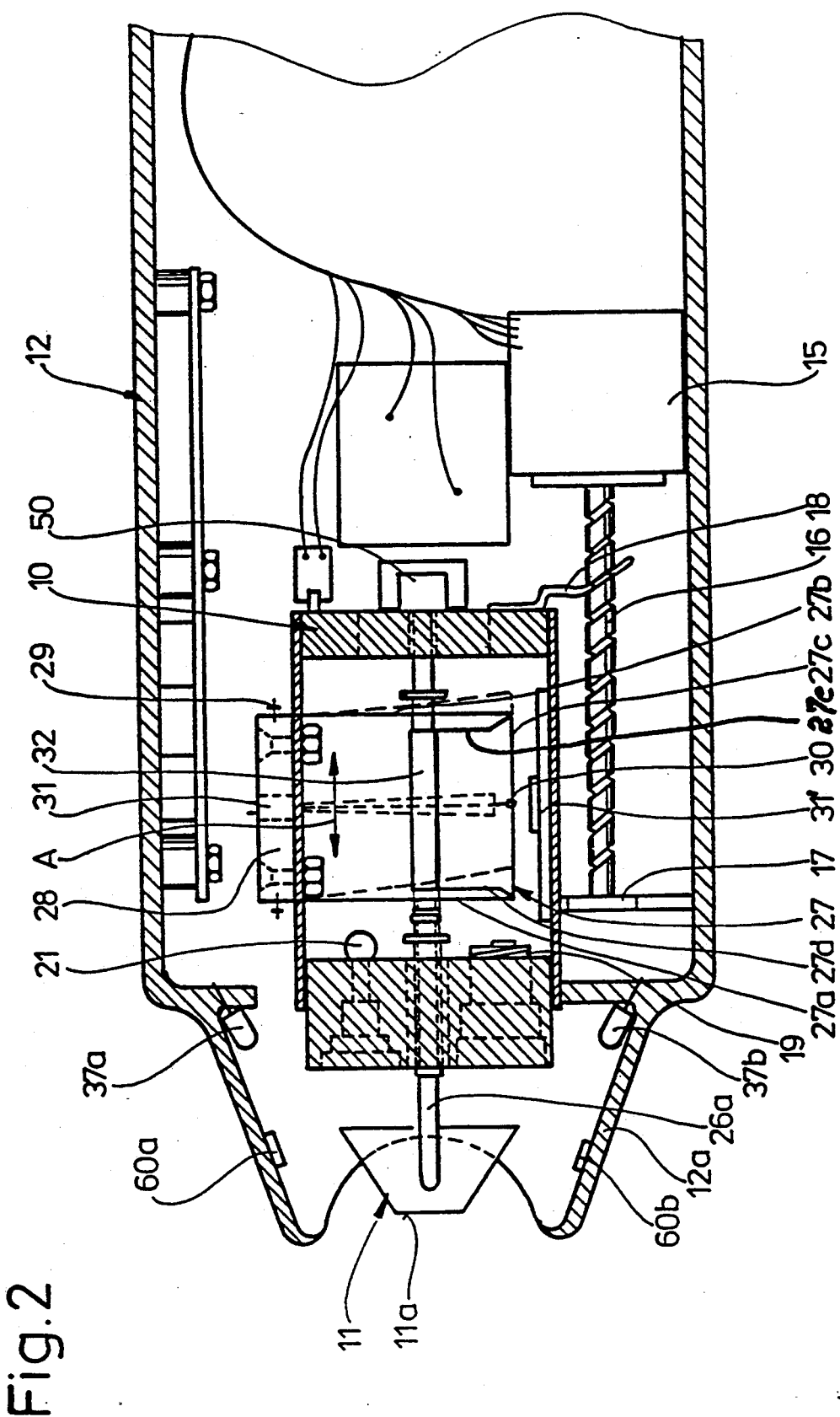
FIG. 2 also shows a longitudinal section of the embodiment according to FIG. 1, rotated 90°, taken along Line II—II in FIG. 1.
Figure 3:
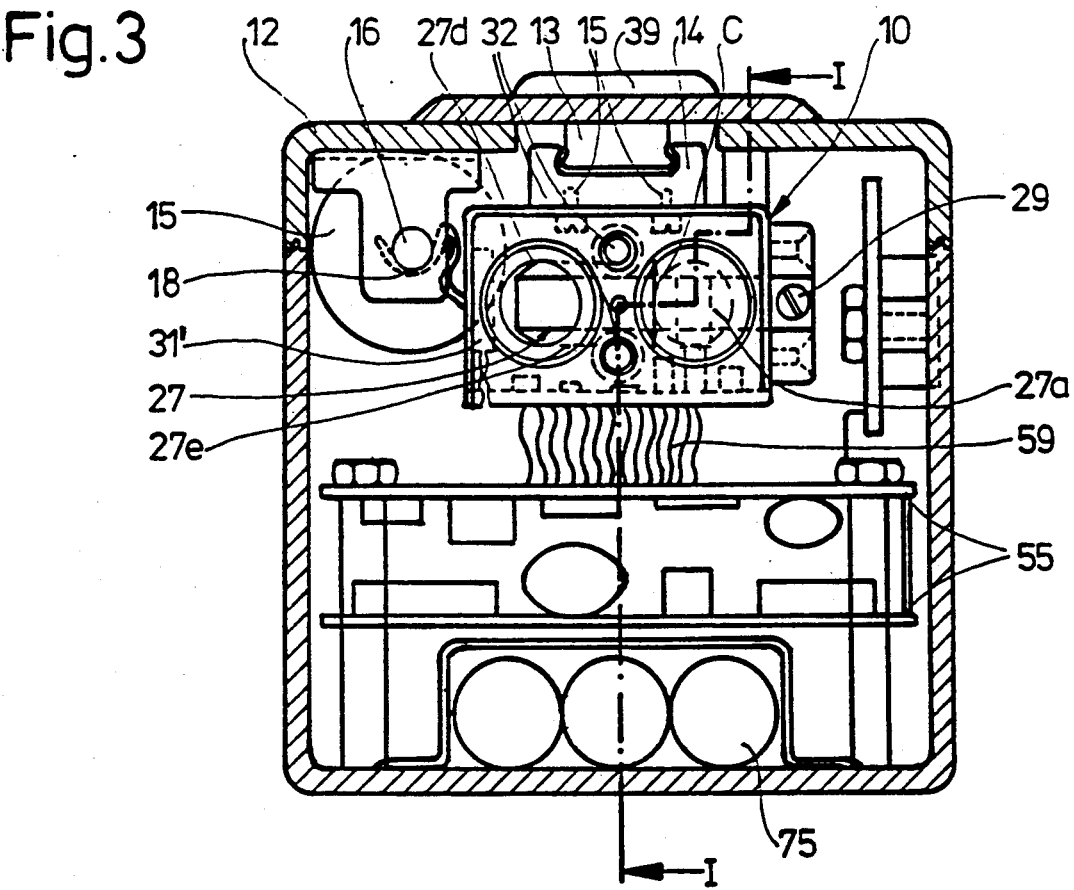
FIG. 3 shows a cross section of the embodiment according to FIGS. 1 and 2, taken along Line III—III in FIG. 1.

Consequently, as shown in FIGS. 1, 2 and 3, the present invention incorporates a power-driven slide 10 which, in turn, mounts the measurement member, which is disposed slidably relative to slide 10 under the effect of spring force, with the measurement member being denoted prism 11 in the figures. With prism 11 in a stationary contacting relationship against the eye, the pressure can be continuously increased by shifting the slide, while simultaneously performing an optical measurement of the respectively achieved aplanation diameter and the force that gradually increases from the reaction of the spring mounting of the prism, incorporating the spring rate curve to be determined, preferably also by means of an optical measurement method. In this connection, the detailed design of a preferred practical example of a measurement apparatus of this type (tonometer) for obtaining multiple measured values is as follows.

Slide 10 is slidably mounted in a suitable manner to the surrounding housing 12 of the tonometer; in the illustrated practical example, as can best be seen from the representation shown in FIG. 3, this is accomplished by means of a guide rail 13 which is fixedly attached to the housing, guide rail 13 being surrounded by a sliding member 14 which is suitably retained on slide 10, for example by means of screws 15. The respectively complementary configuration of guide rails 13 and sliding member 14 can be of dovetail-like design, whereby linear guide means would naturally also be possible here, which need not be discussed in any further detail. Consequently, slide 10 is therefore able, as shown in FIG. 2, to execute a relative shift within the housing in the direction of double-headed arrow A, the relative shift being accomplished under the effect of power drive means, for which purpose an electric motor 15 is disposed in the illustrated practical example. Electric motor 15 drives slide 10 via an output spindle 16 with an opposite bearing at 17 in that a guide member 18, preferably in the form of a spring, which is stationary on slide 10 and engages the thread of spindle 16. It is obvious that the drive or feed of slide 10 could also be effected through other transport means, such as via a pull cable, preferably pretensioned by means of compensating springs, which would also enable the transmission of structure-borne noise to be avoided.

Slide 10 then further carries the area measurement means (for the respectively aplanated area of the eye), the force measurement means through which the force with which prism 11 presses against the eyeball can be determined, as well as a possible embodiment of a positioning system in order to be able to properly position the prism relative to the eye.

Figure 10:
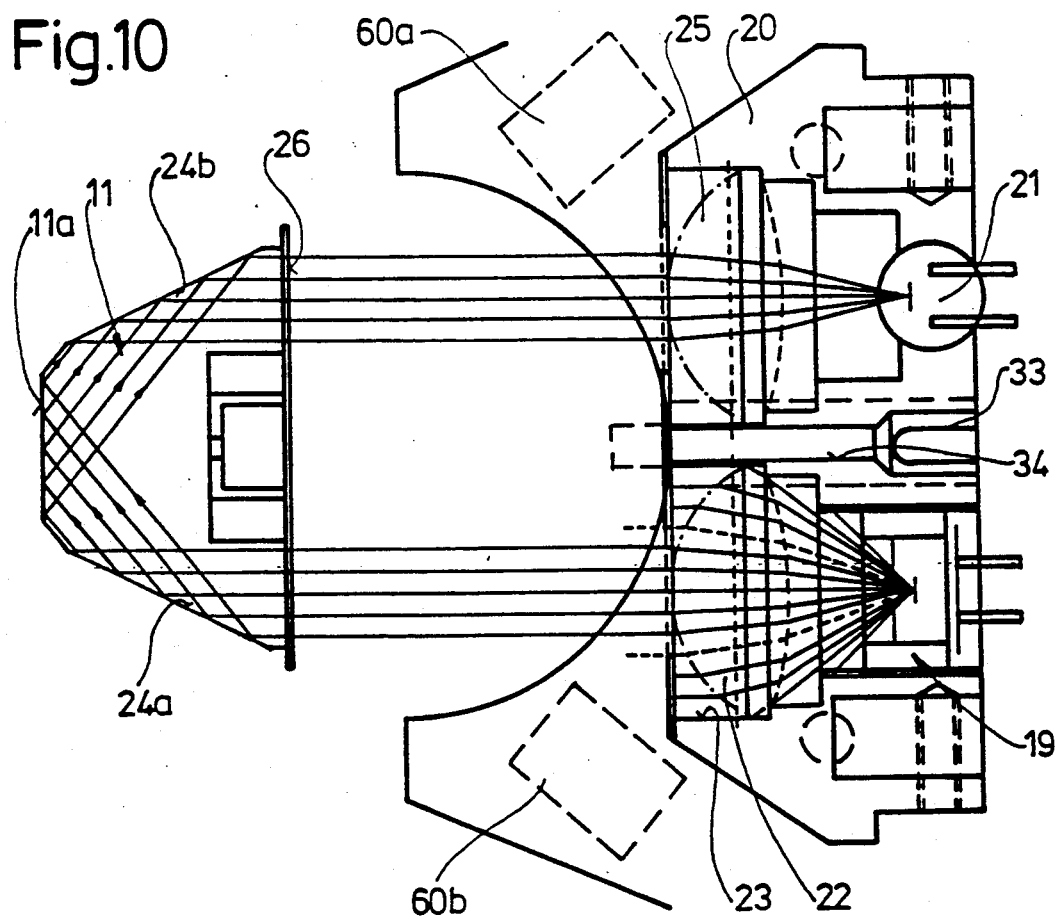
FIG. 10 shows a schematicized representation of the prism measurement member with the lenses, radiation source and radiation receiver associated therewith, in the form of a partial view.

The area measurement means are shown especially clearly in schematicized form in FIG. 10 and, in addition to above-mentioned prism 11, comprise a light transmitter in the form of an infrared light emitting diode (IR LED) for the prism, which is denoted by reference numeral 19 and which is retained in a suitable recess of an optics bearing pedestal 20, together with a light or photoelectric receiver 21, such as in the form of a suitable phototransistor.

The following must be taken into consideration in order to be able to obtain exploitable measurement results at all here. Members whose refractive index is at least twice that of water eliminate the total reflection upon contact with front prism measurement surface 11a, so that it is possible to employ a photometric measurement to determine the area of the aplanated eye. However this necessitates that parallel, homogenous light be produced and emitted by IR LED 19, for which purpose the light transmitter is followed by a non-spherical lens 22 for bundling the rays of light in parallel into a beam, which is mounted in a suitable bearing recess 23 of optics bearing pedestal 20. From lens 22, the the light returns to photoelectric receiver 21 through multiple refraction on the inclined lateral surfaces 24a, 24b and on front surface 11a of the prism, which is influenced by the reflection properties of the respectively aplanated area of the eye, whereby the light passes through a further non-spherical lens 25, which then again concentrates the parallel beam of light on the photosensitive area of the phototransistor. Consequently, lens 25 acts as a condenser lens for the subsequent photoreceiver, which can naturally also be a suitable photodiode.

Alternatively, if desired, it is also possible to affix a photoelement having a surface area of appropriate size directly to the prism, such as in the area of the rear surface 26 (FIG. 10), which would then necessitate that corresponding electrical leads preferably be run along the prism holder. In fact, in the illustrated practical example according to FIGS. 1, 2, 3 and 10, measurement prism 11 moves relative to optics bearing pedestal 20, which is fixedly attached to slide 10 in a stationary manner and is carried by slide 10 (FIG. 1). Because the radiation is kept parallel with the aid of non-spherical lenses 22, 25, this does not result in any measurement errors.

In view of an arrangement of a photoelectric element directly on the prism, it is immediately noted that the thin electrical leads that are used in such a construction, can also produce a change in a spring rate curve for the spring 27 in the range of measurement with the apparatus. Such a change in the spring rate can then be readily taken into consideration in the software as a constant factor in calculations. Where a photo element is used directly on the prism, the thin electrical leads are run via a prism holder and the measurement spring on which the prism holder is mounted.

In and of itself, the basic function of the area measurement means (for aplanation of the eyeball) which is designed in this manner is described in above-cited German Patent Disclosure Document 3,818,434 and is based upon total reflection being present on the front surface of the measurement prism for as long as front surface 11a thereof is not in a contacting relationship with the eye. As soon as the contact is then made—here it is then also necessary to take into consideration the influence of tear fluid, which will be discussed below—the reflected volume of light increasingly reduces with increased contact of the prism against the eye and a correspondingly increasing aplanation area, so that it is possible to determine the respectively achieved aplanation diameter following prior calibration. Consequently, the area of the human eye that is aplanated against the prism relates to the volume of light received by photoelectric receiver 21, since, as mentioned above, reflection is reduced and the light disperses away from the prism in an oblique angle in the case of an aplanation. This reduction that is measured by the IR receiver produces a dimension for the aplanated area.

In order to be able to continuously determine the respectively correlated values of force and aplanation diameter, prism 11 is spring-suspended in slide 10 and, as the feed of slide 10 is advanced by the power drive, prism 11 with its bearing is increasingly pushed back against the force of its suspension spring in the same manner, causing this force to increase.

To mount prism 11 on the slide, its top and its bottom surfaces are therefore fixed to a prism holder, as can best be seen from the illustration in FIG. 1, which comprises an upper bearing tube 26a and a lower bearing tube 26b in the illustrated practical example. Bearing tubes 26a, 26b extend both through optics bearing pedestal 20 as well as, according to a preferred practical example, through a rear terminating wall 20' of slide 10 and are suspended on the slide merely by a special measurement spring, however are otherwise freely slidable and, to this extent, absolutely free of friction, as well. This measurement spring, whose design will be discussed immediately below, then operates conjointly with a position sensor, through which the pressure applied to the human eye can be measured. In other words, it is the slide which, initially (processor-) controlled by a stepping drive motor, brings the prism into the measurement position and then, as the drive continues, produces the relative shift between it and the measurement prism via the spring suspension means, thereby enabling the force measurement to be made, which occurs simultaneously with the above-described area measurement though aplanation of the human eye. During this measurement, the prism has then virtually come to a standstill, and the force acting upon the eye, which is therefore increasing, is produced by the measurement spring, as translated from the continuing motion of the slide.

In the simplest case, this force measurement can be performed by determining the additional component of force to be applied which is produced by the further movement of the slide when the prism has come to a standstill; however, since a plurality of unacceptable other effects (friction, etc.) would also play a role here, it is suggested, according to a preferred characteristic of the present invention, that the pure force exerted by the measurement prism be determined exclusively in that this force is determined through the deflection of the measurement spring, with consideration being given to the known spring rate constants.

Although, in principle, the spring employed in this connection could be of any desired design, it is preferred that the spring be designed in the nature of a parallelogram, so that measurement spring 27, as can best be seen from the illustration in FIG. 2, has two main legs 27a, 27b which are fixed to the slide by means of a bearing pedestal 28, for example through lateral screw fasteners 29, as can best be seen from FIG. 3. Main legs 27a, 27b extend perpendicular to direction of motion A of slide 10 and unite to form one piece via a base connector 27c. Also disposed on this base connector is a type of slit diaphragm 30 or another type of suitable aperture, through which light falls from illumination means which are also arranged in bearing pedestal 28 to form a positioning system—as will be discussed further below.

Also extending upwardly and downwardly, in the plane of the drawing, i.e. on either side, from base connector 27c of single-piece measurement spring 27 are additional single-piece bearing legs 27d, 27e, having a width that corresponds the length of base connector 27c and which are swung back by a specified length toward main legs 27a, 27b to upper and lower bearing tubes 26a, 26b for measurement prism 11, which extend through at this point, and are connected therewith at this point in that, for example, they surround bearing tubes 26a, 26b, at 32, as shown in FIG. 3.

This produces precise linear guide means for the prism holder (through tubes 26a, 26b) as a result of the parallelogram guidance of measurement spring main legs 27a, 27b, as well as the force measurement means for the spring shift via base connector 27c. This is based upon the underlying principle of a position sensor, implemented through an IR transmitting diode 31 and a light receiver 31' on the opposite side of the interior wall of the slide, between which slit 30 of measurement spring base connector 27c is arranged. Viewed in its own right, a light-optical arrangement of this type incorporating a shifting motion—with the deflection of measurement spring 27 being termed the shifting motion here—is known, whereby light receiver 31' can be a photoresistance element of large surface area, which gives off a correspondingly different electrical current, depending upon where the light from transmitting LED 31 falls through slit diaphragm 30 of measurement spring 27'; in professional circles, light receivers of this type are customarily termed PSD elements and will continue to be so designated below. It is therefore possible to determine the possible deflection of the measurement spring parallelogram, which is suggested in dash-dotted form in FIG. 2, through the changes in position of slit diaphragm 30 via PSD element 31' and to convert them into force values in the associated analysis means (microcomputer), which are then associated in tabular form to the area values of the aplanation, which are handled in the form of addresses, for example, to implement the aplanation function in the form of a curve.

Figure 12:
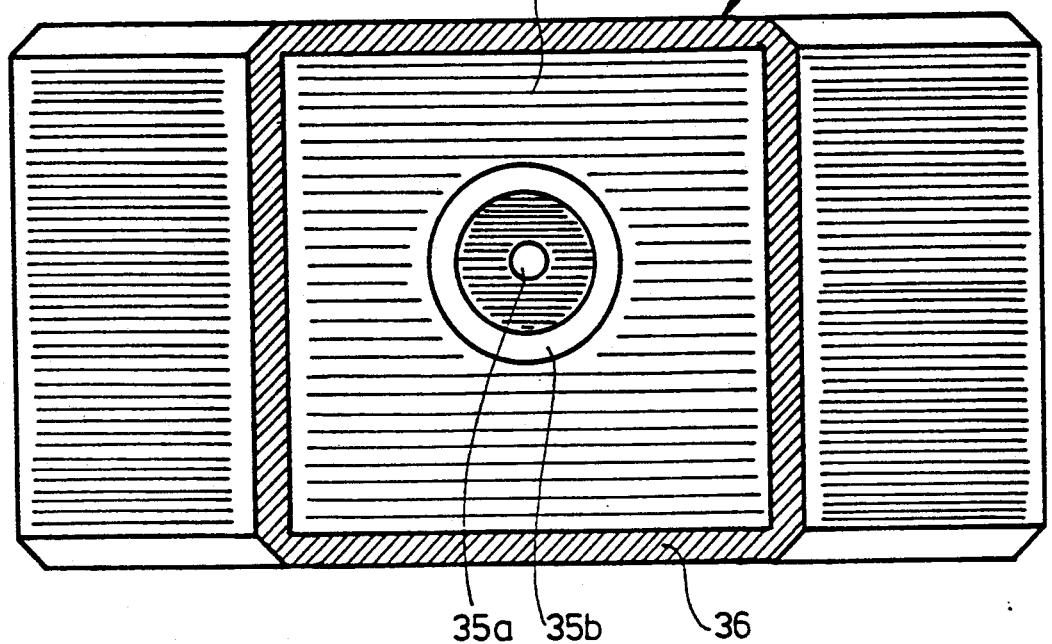
FIG. 12 shows the same prism in a view from the front, illustrating blackened partial areas to simplify positioning in front of the examinee.

Finally, since they are also mounted on the slide, first positioning means are also included in this area; these first positioning means are employed to highly accurately position the entire measurement apparatus, including the measurement member, i.e. prism 11, in front of the eye and aimed at it in such a manner as to permit the measurement to be performed in the desired manner and with a correspondingly high degree of accuracy. In the case of these first positioning means, the device is positioned in front of the eye with the aid of a suitable light source 33, such as positioner LEDs which, as shown best in FIG. 10, are also additionally mounted in optics bearing pedestal 20, specifically on the axis of the surface normal of measurement prism 11. From this positioning LED, (pulsed) light then falls on the cornea, i.e. the surface of the eye, through measurement prism 11, with this light first passing through a special structure on the measurement member (prism 11) before falling into the eye. This special structure can best be seen from the illustrations in FIGS. 11 and 12; with the blackening of two lateral prism surfaces 11b and 11c, as well as rear surface 11d formed by a hollow in the practical example according to FIG. 1, facing away from the eye, in this case the structure comprises two concentric circles, 35a as the inner circle and 35b as the outer circle. The blackening of lateral prism surfaces 11b and 11c, as well as of rear prism surface 11d, whose width and height generally correspond to the dimensions of front surface 11a of the prism, produces a completely blackened structure of the measurement prism for the viewer, as shown in FIG. 12, with all visible surfaces, as suggested by the special shading, remaining black with the exception of concentric circles 35a, 35b, which are illuminated by the positioning LED. In this manner, as a result of the recognizable differences in brightness and the configuration of the figure that is viewed (concentric circles), it is possible to position the device, even if only a limited portion of the field of vision is available, as it is merely necessary to advance the device to the eye whose intraocular pressure is to be determined in such a manner that concentric circles 35a, 35b always appear to be fully illuminated when viewed with this eye. The reason for the possibility of performing fine positioning in this manner is that light source 33 can be seen through concentric circles 35a, 35b, however only if the light source, the center of the circle and the optical axis of the direction in which the eye is looking are in alignment. Consequently, both the intensity of the light as well as the correct shape of the circles, as they are seen from the eye, decline if positioning is not correct. This enables fine adjustment which, in conjunction with a further positioning aid, enables the device to also be employed with examinees whose field of vision is partially obscured or who have highly dilated pupils, as a result of medication, for example.

Figure 11:
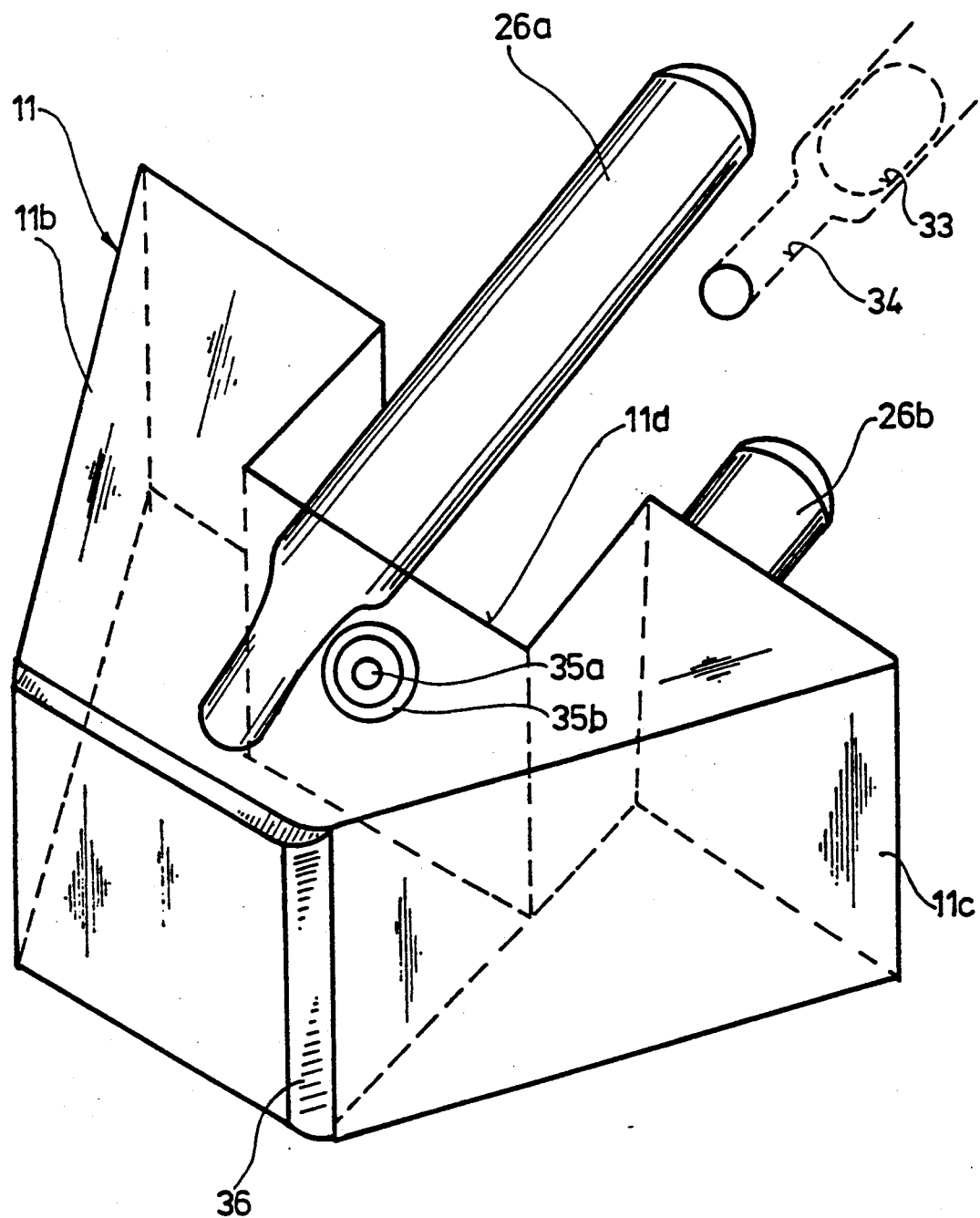
FIG. 11 shows a perspective representation of a possible embodiment of a prism serving as the measurement member, with components for mounting.

A second positioning aid consists of the peripheral border of front surface 11a of measurement prism 11 being matte and being able to have a broken peripheral edge 36 (FIGS. 11 and 12). Moreover, separate, additional illumination sources are disposed, which are denoted 37a, 37b in FIG. 2 and which, if desired, can also transmit rays of light, such as green light. Consequently, this matte border, illuminated in green, for example, enables initial coarse adjustment, whereby central light source 33 disposed in the axis of the surface normal of measurement prism 11, in conjunction with the blackening and the special optical structure, enable fine positioning both with respect to the alignment of the measurement apparatus relative to the eye as well as with respect to the angle of inclination. In this connection, concentric circles 35a, 35b are not illuminated by the light from additional illumination source 37a, 37b, with differentiation also being possible as a result of the different colors of the light sources.

The additional illumination serves a further purpose, namely to narrow the pupil as a result of the additional light that falls into the eye, thereby making positioning with the aid of the concentric circles even more exact.

The basic measurement procedure is then as follows. First, the tonometer is activated by means of a master switch 38 disposed on the front side of the device, and the measurement process is then initiated by briefly pressing a start/stop pushbutton switch 39 disposed on the top of the device. Positioning light emitting diode 33 and additional light emitting diodes 37a, 37b then begin to illuminate; the tonometer is advanced to the eye and positioned.

Start/stop pushbutton switch 39 is then held depressed; positioning LED 33 flashes briefly and slide 10 advances; a measurement having a maximum duration of 5 seconds is then performed—the exact measurement procedure will be discussed separately below; positioning light emitting diode 33 then briefly flashes again, the slide retracts, and the tonometer moves away from the eye. The measured value can then be read immediately on a digital display in a suitable location on the panel of the housing, and a further measurement process can than be initiated, if desired, or the tonometer can be switched off again. Moreover, positioning means in a further sense are also disposed, of which a first embodiment is illustrated in FIGS. 13 and 14.

Figure 14:
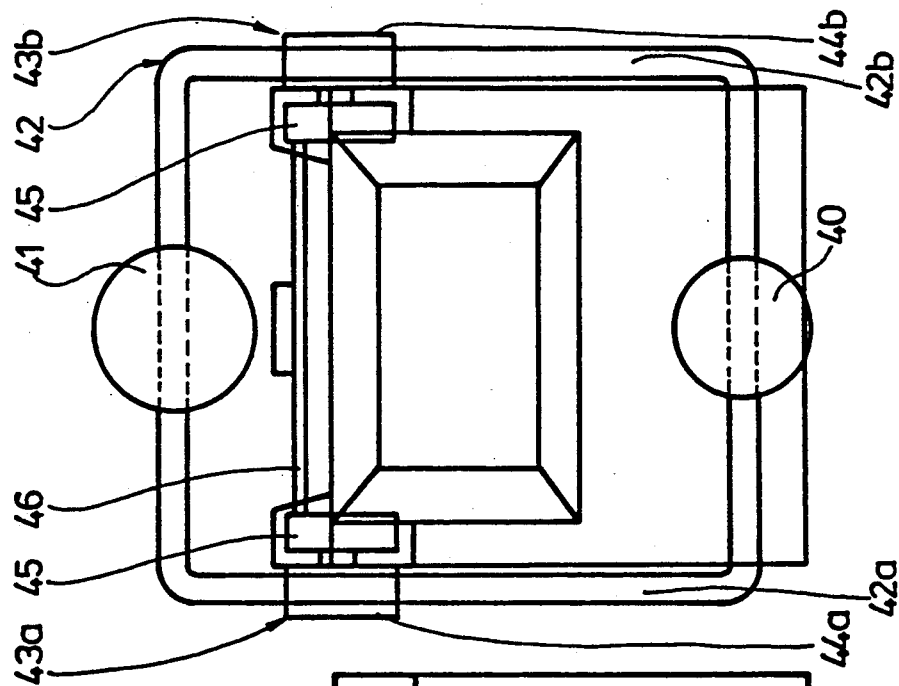
FIGS. 13 and 14 show highly schematicized representations, in side and front views, of a universal head support, controllable by a computer or through manual operation, on the housing of the tonometer according to the present invention.
Figure 13:
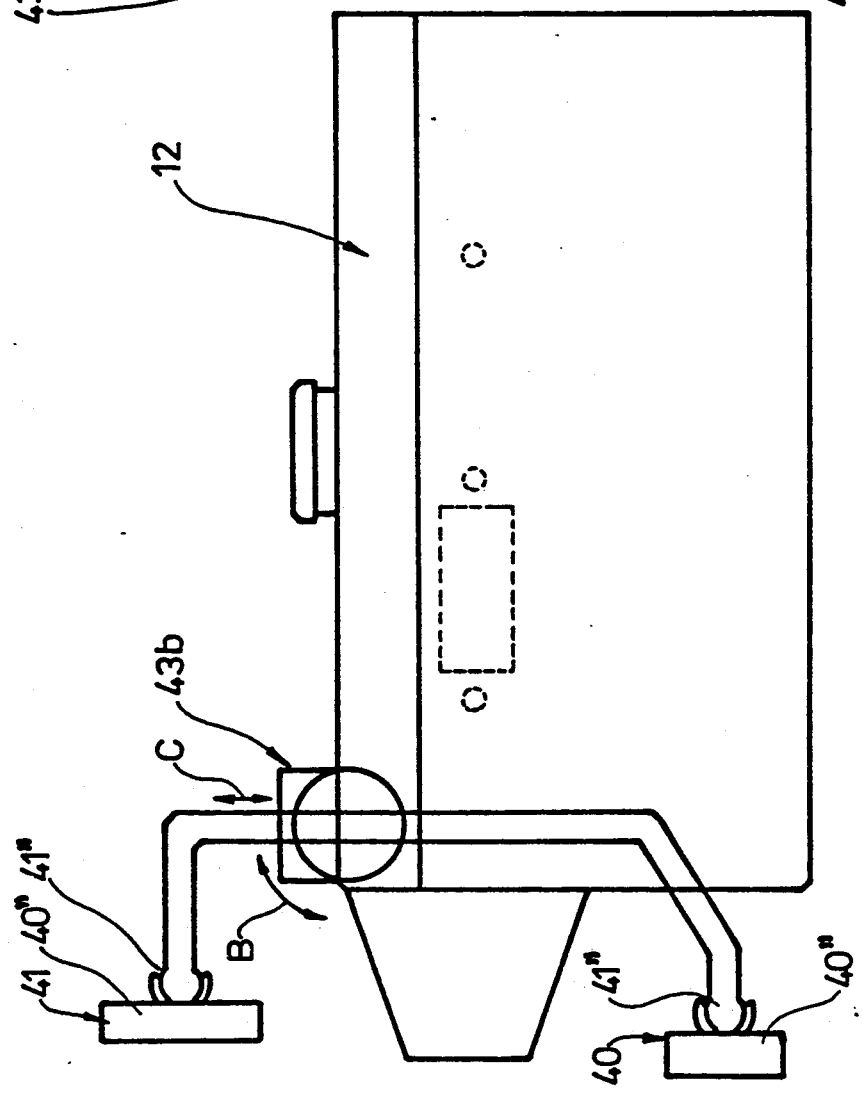

Since it is difficult to position the device in front of the eye merely by holding it firmly with the hand, head supports are disposed on the device, each of which, according to FIGS. 13 and 14, comprises a cheek support 40 and a forehead support 41, for example.

It is practical to mount both supports 40, 41, which can also comprise suitable padding, by means of a common, enclosed bow 42 which, as shown in FIG. 14, can be of rectangular basic configuration and can be fixed to housing 12 of the tonometer on both sides thereof through bearing means 43a, 43b. Bearing means 43a, 43b can be designed in such a manner that lateral bow legs 42a, 42b are guided by sleeves 44a, 44b which, in turn, are pivotally mounted on housing 12 as shown by arrow B, whereby both legs 42a, 42b of mounting bow 42 for the cheek and forehead supports can also be shifted in a direction from top to bottom as shown by double-headed arrow C. Arresting means 45 can then be additionally associated with guide sleeves 44a, 44b; arresting means 45 can comprise screwing means, for example, so that it is then possible to both clamp the bow legs firmly in the sleeves and arrest the sleeves in their respective angular positions relative to housing 12. This results in secure positioning and fixation of housing 12 of the tonometer in front of the eye, whereby it is obvious that arresting means 45 can be actuated by a common, manually actuated clamping rod 46, or clamping of the forehead and cheek supports in the desired position can then be effected by the existing microcomputer through appropriate control if, on the basis of the data supplied to it, the microcomputer recognizes that the tonometer is in the correct position—This will be discussed below with reference to organization of the microcomputer that controls the procedures of the tonometer.

Figure 15:
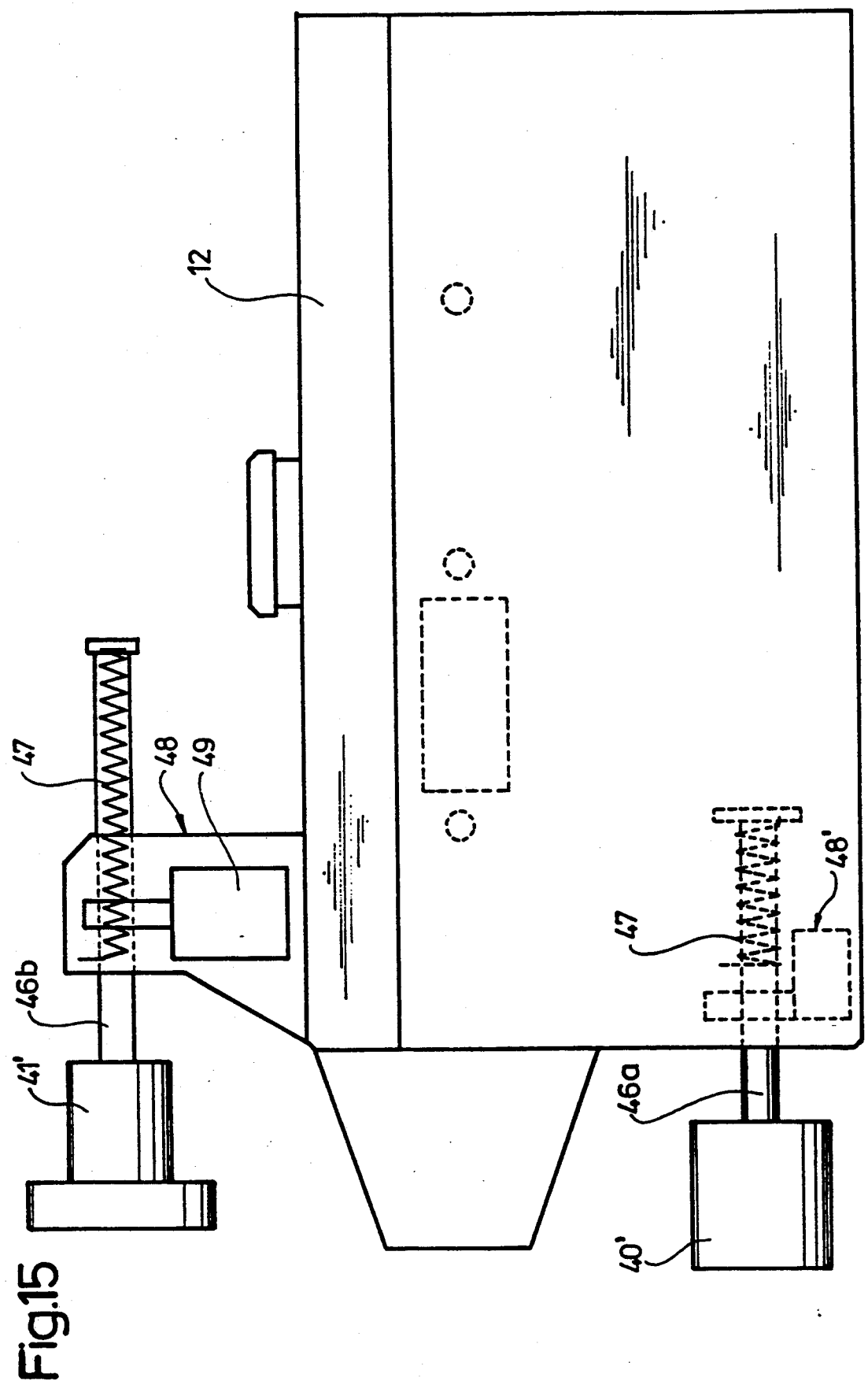
FIG. 15 shows a further embodiment of a computer-controlled head support.

An alternative embodiment of supplementary positioning means, which can also be controlled by the microcomputer, is illustrated in FIG. 15. In this practical example, cheek support 40' and forehead support 41' are mounted independently one from the other on housing 12 of the device, namely by means of bearing tubes 46a, 46b, which are shiftably mounted under the pretensioning of soft draw springs 47 in bearing pedestals 48, 48' which are attached to housing 12, for example. At the same time, these bearing pedestals also contain clamping means 49, which can be suitably activated and controlled by the computer, so that when the inclination-free, aligned position of the device in front of the eye has been attained and recognized by the computer, the forehead and cheek supports are clamped firmly in place, so that the measurement process can then begin.

In connection with these additional positioning means, it is therefore essential for both supports for forehead and cheek to be adjustably designed and able to be moved through minor spring force in such a manner as to reduce the desired clearance between eye and device, or measurement means, when the device is advanced, with draw springs 47 ensuring contact of the supports on the face of the examinee until the end position has been reached, whereupon the supports are clamped firmly in place.

In addition thereto, the positioning support means shown in FIGS. 13 and 14 additionally enable the housing of the device to be moved along a specific path about the eye, as defined by the bow, when the two contact plates 40'' which form forehead and cheek supports 40, 41 are in a contacting relationship with the head. In this connection, the two contact plates are preferably mounted on the bow by means of ball joints 41''. Nodding the device about the bearing point as an additional degree of freedom is then ensured through the pivotability of guide sleeves 44a, 44b.

Further disposed in the device are a plurality of safety means, which are chiefly intended to prevent the occurrence of forces which could be harmful to the human eye during the course of the measurement process.

A first safety means can primarily be implemented in the software in that PSD element 31' recognizes an excessive force through the identified degree of measurement spring deflection, and the corresponding controller signal from the PSD-LED is employed to recognize an overload, which can then consist of reversing the sense of direction of the drive motor for slide 10, which is preferably designed as a stepping motor.

Moreover, a special overload switch 50 (FIG. 1) is also disposed which, connected in series with the motor control, switches off the electrical current to the motor directly. Overload switch 50 is designed in such a manner that it is arranged in the area of penetration of one of the bearing tubes for measurement prism 11, lower bearing tube 26b in the case of the illustrated practical example, by means of an appropriate hole 51 in rear terminating block 20' of the slide. If measurement prism 11, and thus one of its bearing tubes 26b, is therefore pushed back far enough against the effect of the measurement spring bearing that the rear end of the tube can actuate plunger 50a of overload switch 50, electrical current to the motor is switched off immediately.

In this connection, the spring travel (switch travel), as well as the spring force required for actuation of overload switch 50, can be employed as an additional message or warning to the user.

Figure 9:
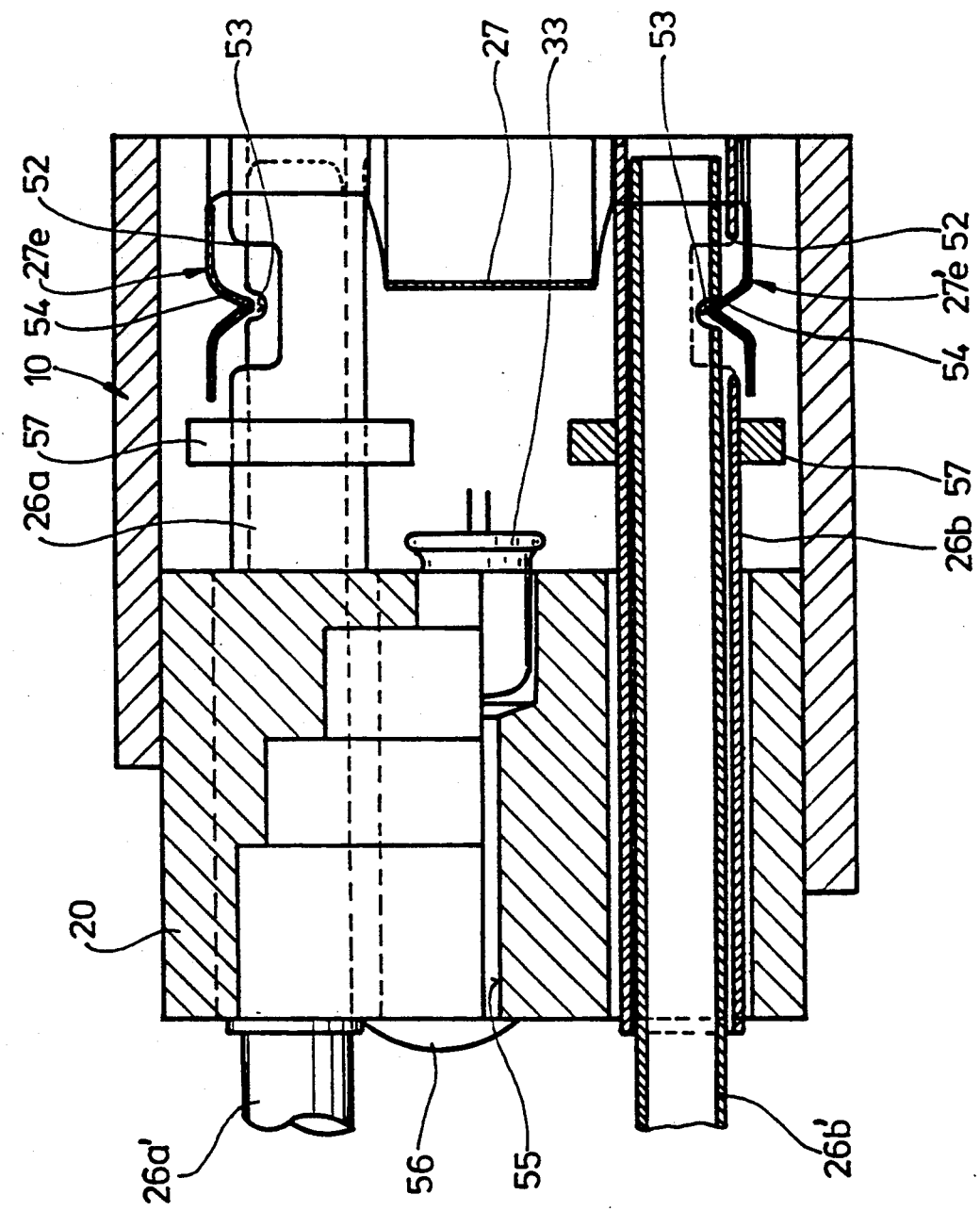
FIG. 9 shows area X in FIG. 1 on a larger scale.

In the present invention, a further safety means of a purely mechanical nature consists of the tube bearing of the measurement member, i.e. prism 11, being designed in the form of telescoping suspension means, as can best be seen from the illustration in FIG. 9, which shows area X of FIG. 1 in greater detail.

Consequently, each of the bearing tubes comprises an outer bearing tube portion 26a, 26b, with an inner bearing tube 26a', 26b' being slidably retained therein in a telescoping manner and also being fixed in a given position, so that the two pairs of tubes, one inserted in the other, of the prism holder can normally always be shifted as a unit relative to slide 10 as a result of their spring mounting.

In this connection, fixation of the two telescoping tubes one relative to the other is effected with the aid of pretensioned springs, each of which, as shown in FIG. 9, engages a notch or recess 53 in the inner tube with a sharp projection 54 through an opening 52 in each of the outer tubes, whereby these two retaining spring areas are naturally fixed to the outer tubes in a stationary manner. It can be seen that the spring elements which engage notches 53 in the inner tube can not be lifted out of these notches until the force acting in the direction of measurement has exceeded a given force threshold value which can still readily be accepted as a safety threshold value for the user of the device. In the event of this lift-out, there is then a relatively minor shiftable telescoping arrangement of the two pairs of bearing tubes one within the other, thereby releasing the non-positive connection between the two tubes. In this case, the inner tubes which support prism 11 can be slid to a rearward position, along with the measurement member.

A preferred embodiment of this safety aspect consists of the arresting springs also being an element of measurement spring 27 and being able to extend laterally from surround areas 32, with which the measurement spring is attached to outer bearing tubes 26a, 26b. Consequently, the two fixing spring areas which stipulate the relative position of the two bearing tubes, which telescope one within the other, one relative to the other are also designated 27e, 27e'.

The present invention additionally comprises a plurality of further possibilities for optimizing the measurement, initially in the mechanical sector; for example, the tapered front housing area 12a, which surrounds and partially encloses measurement prism 11, can itself either be of ocular-like design or can carry an additional ocular, which can be designed in such a manner that it fully surrounds the outer area of the eye, more or less in the manner of film or video cameras, covers the eye and is in a contacting relationship therewith, thus, in and of itself, producing secure support for the housing of the tonometer, with the forehead and cheek supports of the further positioning means being eliminated, if desired. In this connection, it can be advantageous for an ocular of this type to be pivotally mounted on housing 12 in such a manner that it can be moved freely in all directions, with this free mobility then, in turn, as already discussed above, being able to be arrested by clamping through an appropriate control signal from the microcomputer when the desired measurement position has been reached.

A further advantageous embodiment of the present invention can consist of additionally bundling the light from positioning LED 33, which shines forwardly toward the measurement prism through a very narrow hole 55 in optics bearing pedestal 20, in a suitable manner with a lens 56 being designed in accordance with the desired degree of bundling.

The illustration in FIG. 9 further shows a stop 57, which is arranged in a stationary manner on both of outer bearing tubes 26a, 26b, each being designed in the form of an annular stop; stop 57 is employed to limit excess extraction of the measurement member (prism 11), so that the bearing can not be over-elongated by the measurement spring.

These annular stops, each of which is attached to one outer tube in a stationary manner, operate conjointly with a further mechanical safety means for securing the device during transport, which will be discussed below. Thus, first of all, a limit position switch 152 is additionally disposed, which is electrically actuated in the limit position by returning slide 10 and whose rearward limit position is stipulated through appropriate control via an input on the microprocessor in conjunction with the stepping motor drive. Operating conjointly with limit position switch 152 is a mechanical end stop 153, which is attached to the housing in a stationary manner; upon end stop 153 having come into a contacting relationship on upper bearing tube 26a of measurement prism 11 in the illustration shown in FIG. 1, which, like the lower bearing tube, extends through end plate 20' of slide 10, (outer) bearing tubes 26a, 26b, which are coupled one with the other, are slid far enough forward to bring front annular stops 57 (FIG. 9) into a contacting relationship against optics bearing pedestal 20. This arrests the spring-loaded portion of the measurement apparatus, which is, to this extent, mounted in a freely oscillating manner and therefore sensitive, and stabilizes it for transport, so that cleaning work can also be performed on the prism in this stop position, for example.

In order to also prevent the prism from being slid too far inwardly in its free, spring-loaded mount, it is also possible for an inner stop 154 to be attached to outer bearing tubes 26a, 26b, which comes into a contacting relationship inside with rear terminating plate 20' if the prism is pushed too far inwardly.

The mechanical design of the interior of the tonometer is then mainly completed through its electronic equipment, including microprocessor, for which purpose appropriate circuit boards 155 arranged and mounted in an undescribed manner in the free interior space. Thus, for example, block 156 represents a voltage transformer; disposed in the lower portion of the housing in FIG. 1 is a battery compartment 157, a fuse 158 being arranged farther to the left and leading to master switch 38.

The electrical and electronic components arranged on movable slide 10 are connected with main circuit boards 155 via a flexible power supply ribbon cable 159.

Figure 5:
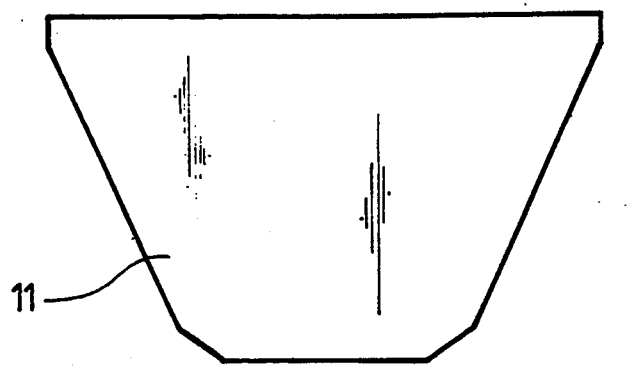
FIGS. 5-8 show possible embodiments of the prisms which form the measurement member.
Figure 6:
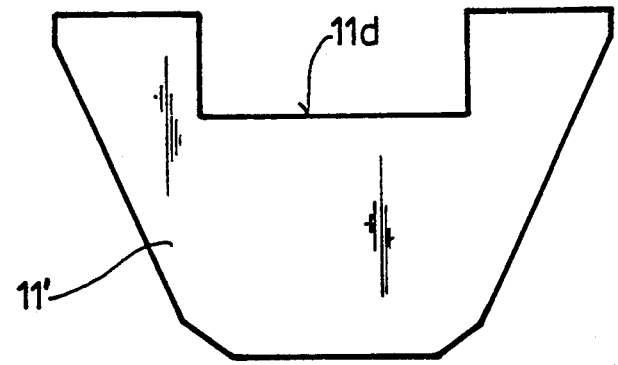
Figure 7:
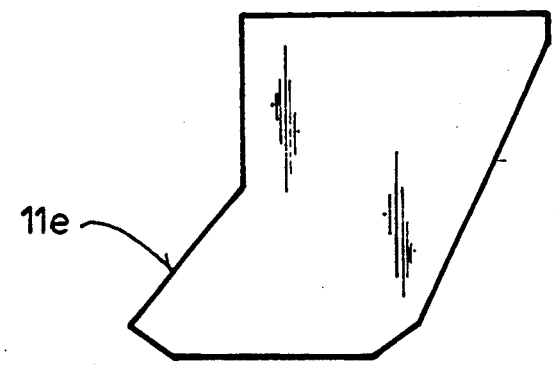
Figure 8:
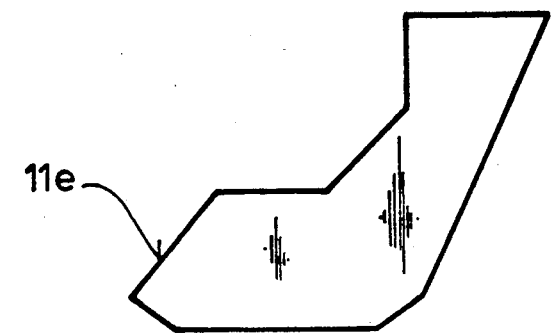

In accordance with the illustrations shown in FIGS. 5, 6, 7 and 8, the measurement prism can be of any desired configuration, whereby the basic configuration of the measurement prism is illustrated in FIG. 5 and designated 11. All embodiments have broken edges to ensure proper functioning of the positioning aid by means of additional illumination means 37a, 37b; measurement prism 11' in FIG. 6 displays the rear cutaway with inner rear surface 11d, which was already discussed above in conjunction with FIGS. 11 and 12, which carries the ring structures; further savings in material with respect to the configuration of the prism result from the embodiments shown in FIGS. 7 and 8, whereby the left-hand portions of the prism have been left away in the drawings. A prism design of this nature is advantageous if a light receiver of appropriately large surface area is arranged directly at the radiation exit wall 11e thus formed and, as already discussed above, its electrical leads are run to the electronic analysis area via the prism holder and the spring legs.

A further advantageous embodiment of the present invention consists of utilizing the light generated by lighting means 33, 37a, 37b to control proximity photodiodes in order to determine the clearance between device and eye. Proximity photodiodes 60a, 60b of this type have narrow opening angles and are arranged on the inside of tapered portion 12a of the housing in such a manner that the desired clearance can be determined in accordance with the triangulation method. The measurement signals from proximity photodiodes 60a, 60b are also advanced to the microprocessor, which employs them, as well, in setting the positioning means (cheek support, forehead support). This can be accomplished in such a manner, for example, that the device is advanced to the eye at the beginning of the measurement, with forehead and cheek supports 40', 41' (FIG. 15) gradually being retracted against the pressure of their soft pretensioning springs until the desired clearance has been achieved on the basis of the triangulation measurement with the proximity photodiodes, whereupon the electronics actuate clamping means 49.

In summary, the safety functions are therefore designed in such a manner that the force acting upon the eye can never exceed 10 pounds, for example, because if the measurement spring is over-elongated, slide 10 retracts under software control due to the response of the PSD element in conjunction with determination of the spring deflection;

with the electrical current to the motor being additionally directly interrupted against the force of a contact spring in overload switch 50 if the measurement spring is further elongated—i.e. this function is not handled by the microprocessor, but is independent of its functions; and finally the prism is mechanically secured by the telescoping arrangement to the extent that, if the frictional force with which the fixing springs fix the normal position of the prism in the notches of the inner tubes is exceeded, both pairs of bearing tubes slide together, one within the other, causing the measurement prism to move away from the eye relative to the slide.

In this connection, it is obvious that the response threshold of overload switch 50 is lower than that of the telescoping safety means; i.e. the overload switch will always respond first and only if the force exerted upon the eye should continue to rise will fixing spring members 27e, 273' slip out of notches 53 and the telescoping mounting means yield.

A significant aspect of the present invention is the possibility of fully automatic execution of the respectively stipulated measurement algorithm, all the way to display of the intraocular pressure following the measurement, in conjunction with all control functions for the mechanical members, a portion of which have already been discussed above, through the association of a microcomputer. In this connection, it is also possible to perform screening-examination measurements and to access the data via a serial interface.

The basic function of the present invention is advantageously based upon the entry of a characteristic curve, which can also be a complete curve, if desired, of a so-called aplanation function by recording a plurality of table values of pressure (exerted force) and aplanation values, which are stored in suitable form and associated one to the other, and then analyzing this characteristic curve, especially in a range which has proved to be especially suitable for measurement of the intraocular pressure, as the most widely varying, and to this extent also known, influencing factors more or less mutually offset one another therein or can be calculated out. A spectrum of aplanation diameters of this type can be located in the range between 2.5 to 4 mm, for example, so that the intraocular pressure can be determined from the slope of dF/dA after the measured values have been recorded, which are grouped as curve I, with statistical fluctuations of appropriate higher or lower variance, around the actual curve II as the characteristic curve of the respectively reached aplanation diameter or the area A of force F. A compensating straight line III is superimposed on the curve produced by the table values for this purpose. In addition, the table that is determined provides further data, namely an area offset $A_o$ in accordance with FIG. 4, which can be a function of the aplanation diameter and is caused by the effect of tear fluid, as well as a force offset, which could be caused by a positioning error; through appropriate design of the software, the present invention is able to eliminate a positioning error of this nature from the very beginning, which will be discussed below, whereby the force offset does not play any role in the equation, as can be seen from the following discussion. The following relationship results from the formation of the differential quotient:

$$p = \Delta F/\Delta A = \frac{(F_4 + F_o) - (F_3 + F_o)}{A_4 - A_{tr4} - (A_3 - A_{tr3})}$$
$$= \frac{F_4 - F_3}{A_4 - A_3 - (A_{tr4} - A_{tr3})}$$

where indices 3 and 4 designate the values of area A and force F with an aplanation diameter of 3 or 4 mm, respectively—$A_{tr3}$ and $A_{tr4}$ designate the area caused by the film of tear fluid with these diameters.

If the change in the area of the tear fluid film in the area under observation is investigated, assuming volume constancy of the tear fluid, which is undoubtedly justifiable in view of the very short measurement period involved, estimated calculations demonstrate that there is virtually no change in the tear fluid in the area under observation. This can be due to the fact that there is a thinner ring of tear fluid with larger aplanation diameters, as in this case the volume of fluid has to distribute itself over a larger circumference. This means that it is not necessary to determine the film of tear fluid in the measurement processes that will be discussed in more detail below, at least not if the desired table values for area and force that are to be determined through the measurement are placed within the aplanation diameter range of between 3 to 4 mm, as the ring of tear fluid has a width of between 0.1 to 0.4 mm in this range and, according to the formulae, the tear fluid areas stand out, whereby the tear fluid areas are generally constant.

Figure 16:
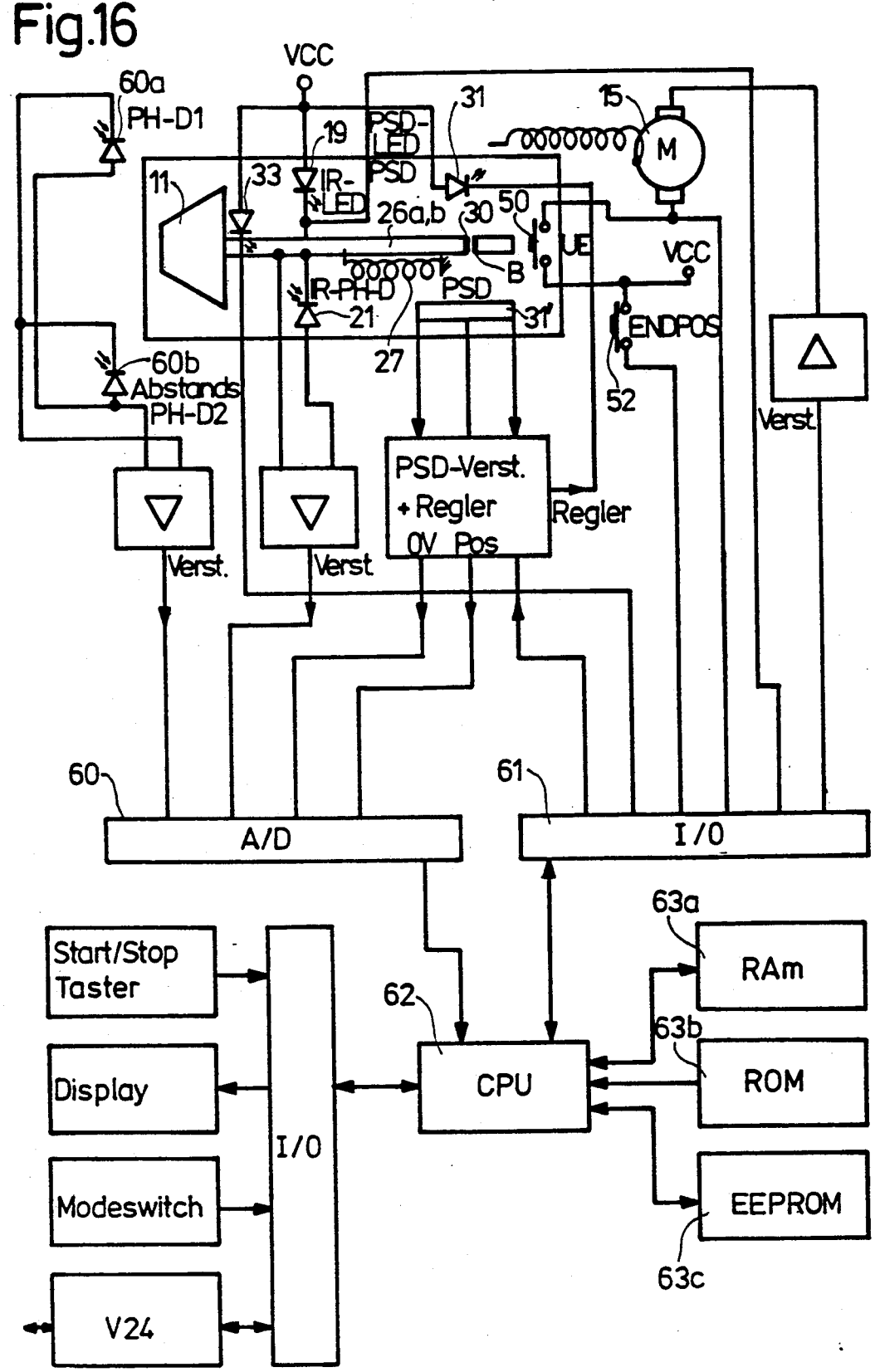
FIG. 16 shows a possible embodiment of the organization of the microcomputer for software analysis of the measured values obtained.

A possible embodiment of the microcomputer/input and output interfaces, its organization, and association with the external circuit elements is shown in FIG. 16, with the reference numerals for the individual elements also being indicated, in addition to the entries, to facilitate understanding thereof.

Arranged in the pure input interface, corresponding to input analog/digital converter 60, are proximity sensor diodes 60a, 60b, the IR sensor for area measurement, comprising IR LED 19 and IR photodiode 21 (cf. FIG. 10), as well as the input data for the overload system and position signal from PSD element 31".

The remaining signal inputs and outputs are connected to the other input/output (I/O) interface 61, including the motor control system. In this connection, three different memory areas are associated with CPU 62 of the microcomputer, namely a RAM memory 63a, a ROM memory 63b, as well as an EEPROM memory area 63c. This is where the longer-term data are stored which the microcomputer needs to ultimately calculate the intraocular pressure from the measured table values that are input.

Figure 4:
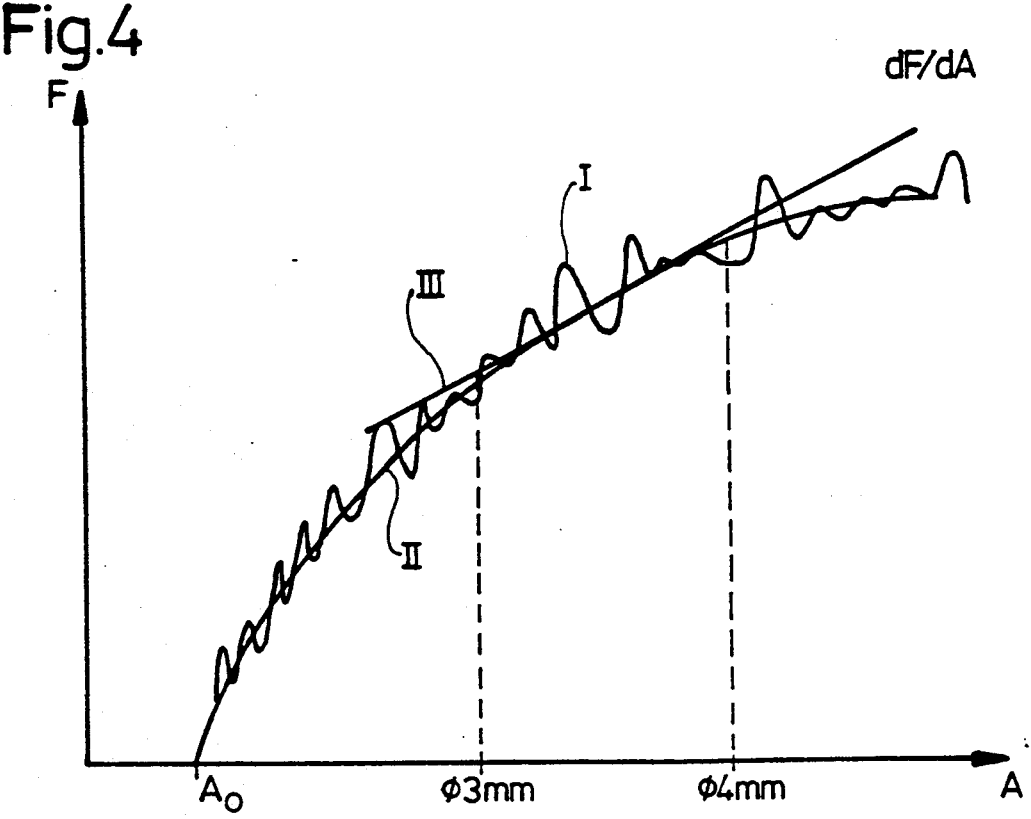
FIG. 4 shows the relationship of the diameter of the aplanated area as a function of the force acting thereupon as a curve in the form of a diagram.

Although this intraocular pressure is determined from the so-called compensating straight line in accordance with curve III in FIG. 4 on the basis of the above-indicated formulae, this compensating straight line is the product of all preceding individual measurements, which are based upon measured value curve I which fluctuates about the average of curve II, with the compensating straight line and its slope being calculated on the basis of all individual measured values which are determined. This means, in other words, that all disturbing influences and peripheral errors are input into the respective measurement result during the respective individual measurements, although, from a statistical standpoint, they average each other out if it is assumed that an appropriate measurement algorithm is being employed in the microcomputer, so that, through the present invention, it is possible for the first time to provide a measurement result which precisely corresponds to the intraocular pressure and does not result from a respective individual measurement, which of necessity always involves some error parameters, which are sometimes not even identifiable.

The memories can be divided up in such a manner that the complete program, including the measurement algorithm, is contained in ROM 63b; while any desired working data, even those of a transient nature, are contained in RAM memory 63a, for example briefly calculated data such as the force offset from the PSD area (which will be discussed below), buffering of the recorded table values; while EEPROM memory 63c can contain characteristic curve data, such as data on the behavior of the PSD element for linearization correction, the value of the spring rate constants of the measurement springs, behavior of the springs under deflection which, due to the parallelogram guidance concept, necessarily represents arc guidance, although of only very minor nature.

And, finally, a possible operating sequence of a measurement process with the tonometer according to the present invention, as it results in the area of the microcomputer, will now be portrayed on the basis of a flow chart for comprehensive information, whereby reference is made to the fact that the individual function blocks indicated therein merely represent a possible embodiment, just as the above description of the preferred practical example does not in any way restrict the present invention.

| | | |
|---|---|---|
| | Start | I |
| | Activate device | II |
| | RAMTEST | III |
| | Warm start | IV |
| | Advance slide | IV' |
| | Determine oscillation period of measurement member Time basis = Period/n | V |
| | Retract slide until limit switch actuates | VI |
| No | No meaningful time found? | VII |
| Take default value | Yes | |
| | Wait for pushbutton pulse 0.2 sec. <t<1 sec | VIII |
| | Activate positioning LED | IX |
| | Wait for START/STOP pushbutton | X |
| Wait 4 sec | Let positioning LED flash twice | XI |
| | Activate IR LED | XII |
| | Determine 100% sensor value | XIII |
| | Stipulate aplanation threshold | XIV |
| | Advance slide | XV |
| Yes | Below aplanation threshold? | XVI |
| | No | |
| Yes | Limit value exceeded? | XVII |
| Retract slide | No | |
| | Wait for time basis | XVIII |
| RESET | Read a value from force measurement means and total until n values have been collected, then write this value to a buffer | XIX |
| | Wait 0.5 sec | XX |
| | Take oldest force value from buffer → Force offset | XXI |
| | Zero the momentary force being exerted | XXII |
| | Measure tear fluid in this state with sensor and store | XXIII |
| | Very slowly advance slide | XXIV |
| | Wait for time basis | XXV |
| | Enter force values in table Aplanated area → Tab position Force value → Function value | XXVI |
| | No Limit value reached? | XXVII Yes |
| No | Apl. area > Amax. ? | XXVIII Retract slide RESET |
| | Yes Retract slide Let positioning LED flash Calculate result and display Warm start | |

It is not necessary to discuss the first five initialization blocks I from "Start" to V, representing retraction of the slide until the limit switch is actuated; function block VI that follows is interesting in that it is designed for determining the oscillation period of the measuring member in the initial state; this is an oscillation which occurs during the measurement and which is at least co-responsible or stipulates the time basis for the oscillation curve of the actual measured values obtained, which fluctuate statistically above and below actually desired characteristic curve II, in accordance with characteristic curve I. When this baseline oscillation period has been determined by the microcomputer, this results in a time basis and the measurement then executes in such a manner that a given number of individual measurements are made within this time basis, which corresponds to one single oscillation of characteristic curve I, for example; to cite a numerical value, which naturally does not in any way restrict the present invention, 16 measurements during an oscillation. In this manner, it is possible to collect enough data on the characteristic curve to then meaningfully determine the slope of compensating straight line I via the range in characteristic curve II in accordance with FIG. 4.

If, according to subsequent circuit block VII, no meaningful time basis has been found, a default value that is based upon the experience from earlier measurements is taken from one of the memories, preferably from EEPROM 63c.

The process then waits until the operator actuates start/stop pushbutton switch 39, whereupon positioning LED 33 activates. If the start/stop pushbutton switch is then pressed and held, it is then caused to flash, in accordance with function block XI; the system then waits again and then activates IR LED 19, which is responsible for determining the area value (function block XXII). The 100% sensor value is then determined, i.e. the volume of light that then falls upon PSD element 31, when there is still total reflection on measurement prism 11, i.e. when measurement prism 11 has not yet come into a contacting relationship with the eye (function block XIII), whereupon an aplanation threshold is then stipulated (function block XIV), which can be located at 97% of the 100% sensor value, for example.

Prior to commencement of the actual measurement, the system then goes into a waiting loop, formed by function blocks XV to XIX, and then goes back to function block XV, "Advance slide," until below the stipulated aplanation threshold, i.e. until the measurement prism has come into a contacting relationship with the eye.

During this waiting loop, limit values can be exceeded which necessitate that the slide be retracted, such as response of the overload switch, over-elongation of the PSD element, etc. In addition, after the time basis has been stipulated (function block XVIII), values from the force measurement means (PSD element 31,) can be read and totaled and written to a memory during this waiting loop. This serves to zero the force sensor (PSD), whereby a plurality of these values can be collected and written to a buffer. This zeroing also enables the consequences of holding the device at a certain inclination to be compensated for, as an inclination of the device results in a shift of the measurement prism if for not other reason than because of the prevailing forces of gravity.

As soon as the reading is then effectively below the aplanation threshold with a given waiting period (function block XX), the influence of the tear fluid is additionally determined and stored in following function blocks XXI, XXII and XXIII, although this is not required for the actual measurement process, as explained above on the basis of the formulae.

Only then does the actual measurement process conclude with function block XXIV (slow slide advance) which, after the time basis (function block XXV) has been supplied, then causes the respective force values determined by the force measurement means to be entered in the table, whereby the area values that are simultaneously determined herefor can serve as addresses, for example. If a force limit value is reached during this measurement (function block XXVII), the slide is retracted and the system resets; if the desired maximum value of the aplanated area is then reached in accordance with following function block XXVIII, the slide retracts and the result is calculated. If not, the slide advances farther forward and the table values are completed.

Since, in accordance with function block XXII, the force momentarily being exerted is zeroed at the moment the aplanation threshold is exceeded, area offset $A_o$, which is based upon force $F = o$ on the tear fluid, results in accordance with the curve of the diagram shown in FIG. 4, at which value the area measurement can begin, depending upon the measurement algorithm upon which it is based, for example, whereby it is also possible and meaningful to record merely the values within the range between aplanation diameters of 3 mm to 4 mm, since, as already explained above, this is where the fewest disturbing factors are present and mutually offset each other.

An alternative embodiment of the present invention additionally consists of attenuating the oscillating capability of the spring-mounted system in a suitable manner, such as by arranging an air chamber in which one wing of the measurement spring moves or by enclosing the measurement spring itself within the area of an air chamber; however it is also possible to provide attenuation in the form of an eddy-current brake, for example through arrangement of a fixed permanent magnet on a moving sheet-metal member which travels with the measurement system.

Additionally of significance in connection with the elastic spring mounting of the measurement member is that no compensating mass is required for the weight of the measurement member and the spring, as the required position independence is achieved in the software in that the zero value is sought and stipulated while the system is oscillating. Moreover, through appropriate circuitry, it is possible to minimize the possible effects of aging in the PSD area or changes in sensitivity by comparing totalling circuits of the entire electrical current given off by the PSD element with a reference value and performing the adjustment on the basis of the brightness of IR light emitting diode 31.

Moreover, a further advantage in the area of the measurement spring results from the fact that it also allows certain deflections perpendicular to the direction of measurement, without the measurement results being influenced thereby. This is achieved through the symmetrical design of the measurement spring, whose two main legs 27a, 27b, as already explained above, extend to the vicinity of PSD element 31' and then extend rearwardly with bearing legs 27d, 27e to the points of attachment on bearing tubes 26a, 26b. This shows that possible shear forces occurring between the measurement surface and the surface of the eye, which are thus deflections perpendicular to the direction of measurement, are tolerable and permissible, as folded-back bearing legs 27d, 27e of the measurement, spring enable motions of this type along double-headed arrow C shown in FIG. 3, with measurement accuracy not being impaired thereby.

The present invention has been described above on the basis of preferred practical examples thereof. Obviously, many modifications and variations of the present invention are possible in the light of the above teachings. It should therefore be understood that, within the scope of the appended claims, the present invention may be practiced otherwise than as specifically described. In particular, individual characteristics of the invention can be employed individually or in combination one with the other.

What is claimed is:

1. An apparatus for determining the inter-relationship between an aplanated area of a human eye and a force required for producing said aplanation, to permit determination of intraocular pressure, comprising:
   a housing;
   a slide;
   a measurement member for placement against the human eye to produce said aplanation in response to the force of said member against the eye, a connection between said slide and said measurement member permitting relative displacement therebetween whereby said relative displacement has a magnitude proportional to the magnitude of said force;
   measurement means connected to said slide for detecting the displacement between said measurement member and said slide and for converting said detected relative displacement into a corresponding force-value signal;
   identification means connected to said slide for detecting the size of the aplanation area produced on the eye by said force of said measurement member, and producing area signals corresponding thereto;
   calculating means for receiving said force-value signals and said area signals and for correlating said signals to determine said intraocular pressure;
   means for moving said slide relative to said housing selectably in a first measuring direction and in a second withdrawal direction, said slide being moveable in a range of linear distances, in use, the size of said aplanated area and said force changing, and said intraocular pressure being determined continuously by said calculating means as said slide moves through said distance range.

2. An apparatus as in claim 1, wherein said calculating means includes output means for providing outputs defining said inter-relationships.

3. An apparatus as in claim 2, wherein, in use, said means for moving said slide continuously advances said slide to provide a continuous increase in force by said measurement member against said eye, said calculating means combining said force-value and area signals into a characteristic curve, said calculating means including means for determining intraocular pressure differentially form said characteristic curve.

4. An apparatus as in claim 1, wherein said measurement member includes an optical prism assembly including a prism, said prism assembly being connected to said slide via a carrying spring, said prism assembly and said carrying spring being fixedly connected in normal use, said carrying spring yielding as said force produced by said measurement member is increased, thereby producing said relative displacement between said slide and said measurement member, said carrying spring being the sole support for said prism assembly, whereby said prism moves relative to said slide by spring deflection without friction.

5. An apparatus as in claim 4, wherein said measurement means includes an illumination member, a photo sensitive receiving element, and a diaphragm with a slit aperture located between said illumination member and said photo sensitive element, said illumination member and said photo sensitive element being affixed to said slide and moving therewith, said diaphragm being affixed to said carrying spring and moving therewith, said relative displacement between said slide and said measurement member causing light from said illumination member to pass through said slit and fall on said photo sensitive receiving element at different positions corresponding with said relative displacement and the force on the eye.

6. An apparatus as in claim 4, wherein said carrying spring comprises two substantially parallel, spaced apart, main legs, each said main leg being fixedly connected to said slide at a respective first end, the second ends of said main legs being connected together by a diaphragm with a slit aperture, a bearing leg extending back from said second end of each said main leg toward said first end of the respective main leg, said main legs being generally perpendicular to said direction of slide motion, and wherein said prism assembly further includes linkage members connected to said prism and extending parallel to the direction of said slide motion, said connection between said prism assembly and said carrying spring being at said bearing legs and said linkage members; and wherein said main legs and bearing legs, said diaphragm, and said linkage members forming a parallelogram suspension system for said prism.

7. An apparatus as in claim 6, wherein there is a pair of said linkage members, each said linkage member includes a pair of carrier tubes, said pair of tubes telescoping one within the other, spring force retaining said tubes in a partially telescoped normal position.

8. An apparatus as in claim 7, wherein the inner carrier tubes of said telescoping pairs each includes a notch and each outer carrier tube of said telescoping pairs has an opening wherethrough said notch is accessible, and said carrying spring includes projections respectively engaging said notches through said openings, said bearing legs of said carrying spring being connected to said outer carrier tubes.

9. An apparatus as in claim 7, further comprising a housing enclosing at least partially said slide and said measurement member, said housing including a guide rail aligned to said direction of slide motion, and said slide including a groove contoured to receive said guide rail therein, a drive motor within said housing having a drive spindle at its output, and a coupling spring connected at one end to said slide and at the other end engaging said drive spindle, rotation of said motor spindle causing said slide to move, selectively, in said first or said second direction.

10. An apparatus as in claim 1, wherein a front portion of said slide, as viewed in said withdrawal direction of said slide, includes an optics bearing pedestal having a central positioning light emitting source, and wherein said measurement member includes an optical prism assembly including a prism and carrier tubes which support said prism, said carrier tubes being parallel and spaced apart, said carrier tubes extending through said optics bearing pedestal in a non-contacting manner, whereby said prism moves relative to said slide without friction.

11. An apparatus as in claim 10, further comprising a housing enclosing at least partially said slide and said measurement member, and wherein illumination members are positioned internally in an area of a forward tapered wall of said housing, and said prism includes lateral surfaces and rearward terminating surfaces, said surfaces being visible by a patient from the front of said housing and being blackened for coarse and fine positioning of said apparatus relative to the eye, said rearward terminating surfaces having two concentric transparent circles positioned in alignment with said positioning light emitting source.

12. An apparatus as in claim 1, further comprising head supports including adjustable forehead and cheek support members connected to said housing.

13. An apparatus according to claim 12, further comprising a tiltable and vertically shiftable bow connected to said housing, said forehead and cheek supports being attached to said bow by means of ball joints, and means for controlled clamping of the positions of said forehead and cheek supports into fixed relationship with said housing, said clamping means being one of manual and computer controlled.

14. An apparatus as in claim 12, further comprising proximity light sources in said housing forming a proximity sensor and operating in accordance with a triangulation method for identification of a clearance between said apparatus and the eye of a person in use of said apparatus, output signals of said proximity sensor controlling said cheek support means by way of said calculating means.

15. An apparatus as in claim 1, wherein said means for moving said slide is a motor, and further comprising a limit position switch which responds to a given rearward position of said slide, said switch interrupting an electrical circuit for operating said motor, and further comprising stops attached to said prism assembly, said stops limiting displacement of said prism assembly relative to said slide by contact with said slide in both said first and second directions of slide motion.

16. An apparatus as in claim 7, wherein said prism assembly further includes linkage members connected to said prism, said linkage members also being connected to said carrying spring for movement therewith, and further comprising an overload switch aligned with one said carrier tube, said one carrier tube in an extreme position produced by said force on said eye, actuating said overload switch, said means for moving said slide being disabled by actuation of said overload switch.

17. An apparatus as in claim 16, further comprising photo optical means for detecting excess deflection of said carrying spring due to said force on said eye, said photo optical means providing a signal to said calculating means to disable said means for moving said slide, and wherein said linkage members each includes a pair of telescoping carrier tubes held in fixed relationship one to the other, excess force on said prism assembly by contact with said eye, unfixing said carrier tubes relative to each other, whereby said tubes telescope to release said force acting upon said eye, said photo optical means operating in response to a minimum amount of excessive force on the eye, said overload switch operating at an intermediate value of excessive force on the eye, said tubes telescoping in response to a maximum amount of excessive force on the eye.

18. An apparatus as in claim 1, wherein said measurement member includes an optical prism, and said identification means including a light source directing light into said prism, and a photoreceptor receiving light reflected within and exiting said prism, the magnitude of reflected and exiting light being proportional to the aplanated area, said photoreceptor providing a signal proportional to said exiting light.

* * * * *